(12) United States Patent
Dean et al.

(10) Patent No.: US 6,433,549 B1
(45) Date of Patent: Aug. 13, 2002

(54) MR BRIDGE SUPPORT

(75) Inventors: David E. Dean, Hartland; David Glenn Lee, Milwaukee; Bruce D. Collick, Madison; Richard Scott Hinks, Waukesha; Michael J. Radziun; Scott T. Mansell, both of Waterford; Donald Elroy Kosak, Menomonee Falls; John Edward Lorbiecki, Hubertus, all of WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/990,667

(22) Filed: Nov. 21, 2001

(51) Int. Cl.⁷ .................................................. G01V 3/00
(52) U.S. Cl. ........................ 324/319; 324/318; 324/320
(58) Field of Search ............................... 324/319, 322, 324/318, 307, 309; 128/653; 335/219

(56) References Cited

U.S. PATENT DOCUMENTS

| | | | | |
|---|---|---|---|---|
| 5,084,676 A | * | 1/1992 | Saho et al. | 324/318 |
| 5,235,283 A | * | 8/1993 | Lehne et al. | 324/318 |
| 5,760,548 A | * | 6/1998 | Frederick | 324/318 |
| 6,160,399 A | * | 12/2000 | Radzium et al. | 324/219 |

* cited by examiner

Primary Examiner—Edward Lefkowitz
Assistant Examiner—Brij B. Shrivastav
(74) Attorney, Agent, or Firm—Quarles & Brady, LLP

(57) ABSTRACT

An apparatus for supporting a patient support bridge member in an MR system where a first end of the bridge is supported by an upright support member on a first side of an MR imaging bore and the bridge extends through the bore so that a second end of the bridge extends out a second side of the bore, the apparatus including a bracket mounted to an MR main magnet on the second side of the bore and extending upwardly to contact and support the bridge there above.

20 Claims, 2 Drawing Sheets

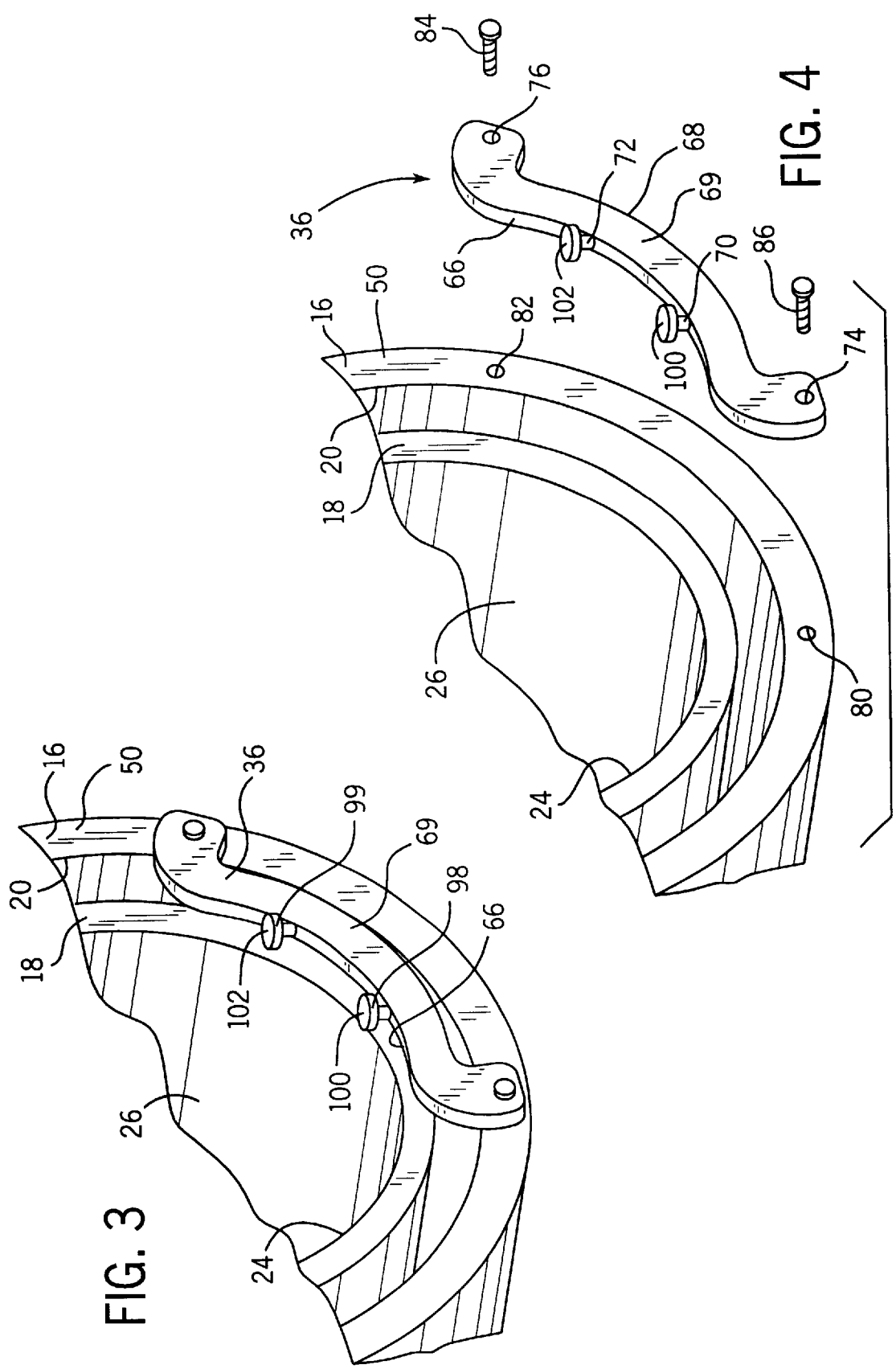

MR BRIDGE SUPPORT

STATEMENT REGARDING FEDERALLY SPONSORED RESEARCH

Not applicable.

CROSS-REFERENCE TO RELATED APPLICATIONS

Not applicable.

CROSS-REFERENCE TO RELATED APPLICATIONS

Not applicable.

BACKGROUND OF THE INVENTION

The present invention relates to MR patient support configurations and more specifically to a patient support that mounts to a main MR magnet and supports a patient table bridge.

An MR imaging system or scanner commonly includes a cryostat, which contains a powerful superconductive main magnet positioned around a main magnet bore. The superconductive magnet is maintained at an extremely cold temperature and produces a strong static magnetic field Bo along a bore axis within the main magnet. Other essential components of the MR system include an RF coil, or RF antenna, and a gradient coil assembly, which comprises a hollow cylindrical structure. The RF coil may be operated in a transmit mode, to generate MR signals in an imaging subject, or may be operated in a receive mode to detect the MR signals.

The gradient coils are electrically excited to impose X-, Y-, and Z-gradient time varying magnetic fields on the primary magnetic fields that are required for imaging purposes. In a common arrangement, each gradient field is produced by a pair or set of gradient coils, wherein each coil is wrapped around one of two cylindrical coil forms. The two coil forms are placed in coaxial relationship, and the coil forms and respective X-, Y- and Z-gradient coils collectively comprise a gradient coil assembly. Arrangements of this type are described, for example, in U.S. Pat. No. 5,570,021, issued Oct. 29, 1996 and commonly assigned herewith to the General Electric Company. Such arrangements are also described in U.S. Pat. No. 5,760,584, issued Jun. 2, 1998 and likewise assigned to the General Electric Company. Typically, the gradient coil assembly is mechanically supported within the cylindrical bore of the main magnet. The gradient coil, RF coil and main magnet together form an imaging area about the main magnet bore axis.

To support a patient within the main magnet bore during data acquisition, a patient support structure is provided that typically includes an upright support, a bridge, a cradle and a bridge support. The upright support is a rigid member that rests on a floor adjacent an MR imaging system within an imaging room and includes an upper end for receiving a first end of the bridge. The bridge includes a stiff member that extends between first and second ends where the first end is mounted to the rigid upright support and the second end extends into and through the imaging area so that its length is generally parallel to the bore axis. In many designs the bridge includes tracks for receiving cradle wheels and guiding the cradle through the imaging area.

The cradle is typically a relatively flimsy member having upper and lower oppositely facing surfaces and a length that is generally sufficient to support a patient. The cradle includes a plurality of wheels mounted to its lower surface and arranged so as to be receivable within the bridge tracks for guidance there along. The cradle is capable of movement along the bridge into various positions with respect to the imaging area including a loading position outside the imaging area and at least one imaging position where at least a portion of a patient disposed on the cradle is positioned within the imaging area.

As configured above, when a patient (especially a relatively heavy patient) is supported on the cradle and the cradle is fully extended on the bridge, the bridge has a tendency to deflect slightly downward thereby causing a patient misalignment. To overcome this problem many support configurations include a bridge support. To this end, an exemplary bridge support includes a rigid member that is typically mounted to the inside of the gradient coil and extends upwardly to and is secured to the bridge relatively closer to the second end of the bridge than the first end. Thus, when a patient is positioned within the imaging area, the cradle and bridge are supported by the upright support on the first end and by the bridge support, gradient coil and main magnet on the second end.

Unfortunately, when a gradient coil is excited to generate magnetic gradients, the gradients interact with structure about the coils and the coils tend to be mechanically displaced (i.e., vibrates). The mechanical structure used to support the gradient coil assembly within the main magnet bore provides a path for transferring or coupling the vibrations of the gradient coils to the main magnet structure. Generally, the main magnet is supported on the floor of the building in which the MR system is operated. Accordingly, the gradient generated vibrations are often directly coupled from the magnet to the floor, and then travel through the floor to vibrate structures throughout the building. As a result, gradient coil vibrations can couple acoustically to rooms outside of the MR scan room, i.e., a room which is specially constructed to house the MR system.

In addition to the problems associated with transmitting gradient vibrations to other facility equipment and space, the rigid bridge support also causes the gradient vibrations to be transmitted to the patient support cradle and a patient thereon. While gradient related patient vibration in early MR systems was relatively minimal and therefore could essentially be ignored, characteristics of newer MR systems have resulted in greater adverse effects. For instance, gradient technology has evolved to the point where relatively high gradient fields are employed during data generation and acquisition so that the magnitude of gradient related vibrations is relatively greater in newer systems. In addition, the actual mass of the imaging components (i.e., the main magnet, coils, shields, etc.) has been reduced appreciably such that even small gradient fields sometimes cause appreciable vibration.

Cradle vibration has two adverse side effects. First, whenever a patient is exposed to a new or unfamiliar medical process, the patient typically and understandably experiences anxiety and nervousness about the experience. This is especially true of MR imaging procedures where noise and essentially uncontrolled gradient movement and vibrations are transmitted to the patient. Anxiety often causes patients to move or flinch during acquisition which can cause image artifacts in images generated with collected data. Second, even where a patient manages to remain essentially still relative to a supporting cradle, where the cradle and patient vibrate together relative to the RF data receiving coils, resulting images are typically polluted by image artifacts.

One configuration that essentially isolates the gradient coils from the main magnet and thereby mitigates transmission of gradient vibrations to the main magnet and surrounding facility equipment and space is described in U.S. Pat. No. 6,160,399 (hereinafter "the '399 patent") which issued on Dec. 12, 2000 and is entitled "Apparatus For Supporting MR Gradient Coil Assembly". According to the '399 patent, two mounting assemblies are mounted to the main magnet and extend axially to the gradient coils, a separate mounting assembly disposed at either end of the main magnet. The mounting assemblies transmit a static force from the main magnet to the gradient coil assembly to hold the coil assembly in place within the main magnet bore in coaxial relationship with the bore and in spaced-apart relationship with an internal bore wall. At the same time, the two mounting assemblies act to dampen or attenuate the gradient coil vibrations, and thus oppose passage transmission of the vibrations through the mounting assemblies to the main magnet. The '399 patent configuration provides no other path through which gradient coil vibrations can be transferred from the gradient coil assembly to the main magnet.

While addressing the problem of transmitting gradient vibrations from the MR configuration to facility equipment and space, unfortunately the mounting assemblies described in the '399 patent do nothing to reduce vibrations to the patient support cradle. In fact, in some cases, by isolating the gradient coil from the main magnet, the end result may be to increase cradle and patient vibrations thereby increasing discomfort and reducing image quality.

SUMMARY OF THE INVENTION

It has been recognized that a patient support table or cradle can be sufficiently isolated from MR gradient coils by, instead of supporting the cradle on the coils, providing a bracket that mounts directly to the MR main magnet and supports the cradle while in an imaging area. This concept is particularly useful where the coil gradient assembly is isolated from the main magnet as in the case of the '399 patent referenced above as the combined coil isolation system of the '399 patent and the present invention increase patient comfort and reduce imaging artifacts appreciably.

An exemplary embodiment of the invention is to be used with an MR system having a main magnet, a gradient coil assembly and a patient support, the magnet having first and second oppositely facing surfaces and forming a bore that extends between the first and second surfaces along a bore axis, the coil assembly disposed within the bore about an imaging area, the support including a support member and a bridge having first and second ends, the support member supporting the first bridge end proximate the first surface, the bridge extending into and through the bore so that the second end is proximate the second surface and the bridge forms an essentially downwardly facing undersurface. The apparatus is for supporting the bridge and comprises a bracket disposed for fixable attachment to the main magnet such that the bracket extends toward the imaging area. The bracket forms at least one essentially upwardly facing support surface for receiving the bridge undersurface and supporting the bridge there above. In several embodiments the bracket is mountable to the second magnet surface.

In one embodiment the bracket includes first and second post members that extend essentially upwardly to distal ends, the distal ends forming first and second upwardly facing surfaces for supporting the bridge, respectively. Each post may include a stainless steel rod having a distal end and a phenolic head member.

In some embodiments the bridge has a width dimension perpendicular to the bore axis, the bracket has a length dimension greater than the width dimension and the bracket is securable to the main magnet at opposite ends of the length dimension so as to have an essentially horizontal orientation.

In most embodiments the bracket components are formed of a low magnetic flux material such as, for instance, a phenolic resin material.

These and other aspects of the invention will become apparent from the following description. In the description, reference is made to the accompanying drawings which form a part hereof, and in which there is shown a preferred embodiment of the invention. Such embodiment does not necessarily represent the full scope of the invention and reference is made therefore, to the claims herein for interpreting the scope of the invention.

BRIEF DESCRIPTION OF THE DRAWINGS

FIG. 3 is a perspective view of the system end illustrated in FIG. 2; and

FIG. 4 is an exploded perspective view of the system end illustrated in FIG. 3.

DESCRIPTION OF THE PREFERRED EMBODIMENT

Figure 1:
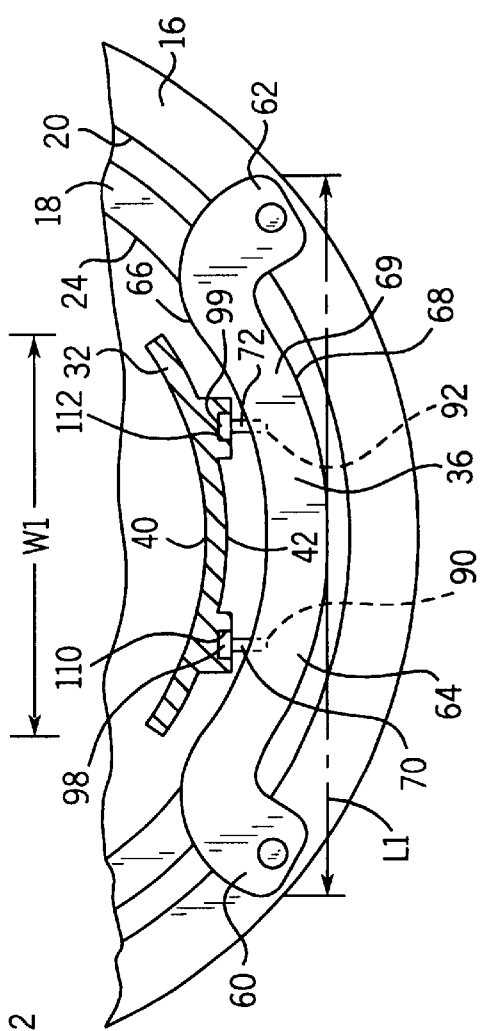
FIG. 1 is a cross-sectional view of an exemplary MR imaging system configured in accordance with the present invention.

Referring now to the drawings wherein like reference numbers and characters correspond to similar elements throughout the several views and, more specifically, referring to FIG. 1, an exemplary imaging system 10 constructed in accordance with the present invention is illustrated. System 10 generally includes two separate sub-configurations, a magnetic resonance (MR) imaging configuration or assembly 12 and a patient support system 14. As known in the MR art, among other components, system 12 includes a large main magnet 16 and a gradient coil assembly 18.

Main magnet 16 has first and second oppositely facing surfaces 48 and 50, respectively, is generally annular in shape and forms a main magnet bore 20 formed about a horizontal bore axis 22 that extends between first surface 48 and second surface 50. Main magnet 16 rests on the floor in an imaging room of a medical facility. Referring also to FIG. 4, main magnet 16 forms two threaded apertures 80 and 82 in a lower portion of second surface 50 that are used to mount a bracket member 69 to surface 50 in a manner to be described in more detail below. In the illustrated embodiment apertures 80 and 82 are symmetrically positioned with respect to a plane (not illustrated) that divides magnet 16 into lateral halves although many other configurations are contemplated.

Gradient coil assembly 18, like main magnet 16, is generally annular in shape and forms an imaging bore 24 about an imaging area 26. Gradient coil 18 is mounted within main magnet 16 such that the main magnet bore 20 and coil bore 24 are concentrically aligned along axis 22. Configurations for mounting assembly 18 within magnet 16 are well known in the art and therefore will not be described here in detail. One exemplary mounting system which is particularly useful in the context of the present invention is described in the '399 patent referenced above which is incorporated herein by reference. Suffice it say here that the '399 patent coil mounting configuration generally blocks gradient coil 18 vibration from transmission to the main magnet 16 while still providing a static force between the main magnet 16 and the coil 18 sufficient to minimize coil motion within area 26.

Support system or assembly 14 includes an essentially upright or vertical rigid support member 30, a bridge or bridge member 32, a cradle member 34 and a bracket assembly 36. Support member 30 has a bottom end 38 and a top end 39. Bottom end 38 rests on the floor of an imaging area and top end 39 extends up therefrom.

Figure 2:
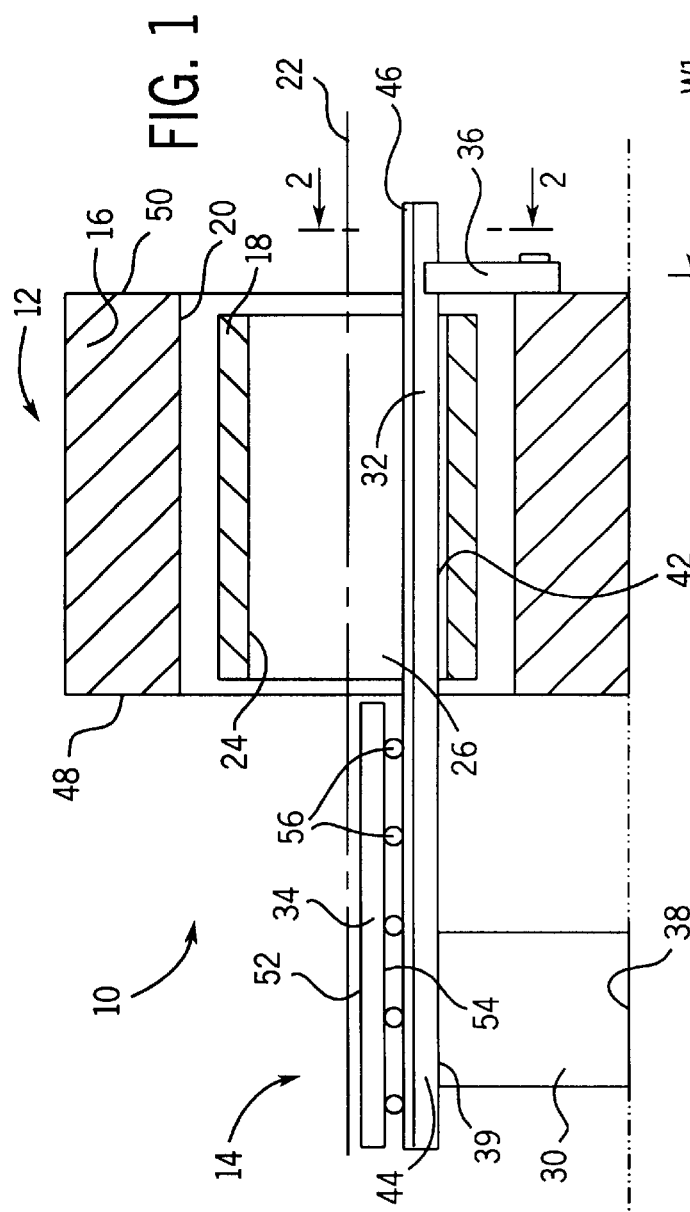
FIG. 2 is a partial cross-sectional view taken along the line 2—2 of FIG. 1.

Referring to FIGS. 1 and 2, bridge 32 is generally an arcuate member which includes oppositely facing top and under surfaces 40, 42, respectively, and extends along a length dimension from a first end 44 to a second end 46. In the illustrated embodiment, bridge 32 has width dimension W1 (see FIG. 2) and is concave along top surface 40. The first end 44 of bridge 32 is mounted to the top end 39 of support member 30 so that bridge top surface 40 faces upward. Support member 30 has a height dimension (not illustrated) such that, when bridge 32 is mounted to top end 39, bridge 32 can extend through imaging area 26 and is supported above the lower most portion of coil assembly 18 (i.e., a gap is formed between bridge undersurface 42 and coil 18 (see FIG. 1)). Support member 30 is positioned with respect to system 12 such that bridge second end 46 extends through bore 24 and protrudes past main magnet second surface 50.

Bridge undersurface 42 forms post receiving recesses 110 and 112 proximate second end 46. Recesses 110 and 112 are generally equispaced along the width W1 of bridge 46 and are proximate lateral bridge edges (see FIG. 2). Operation of recesses 110 and 112 with posts is described in more detail below. Although not illustrated, bridge top surface 40 may form tracks along its length (i.e., parallel to axis 22) for receiving wheels on a bottom of cradle member 34 to support and guide cradle member 34 between various positions described below.

Cradle member 34 is typically formed of a relatively flimsy material having a top surface 52 and a bottom surface 54. Top surface 52 forms a patient receiving surface such that a patient can rest on surface 52 relatively comfortably during a data acquisition session. A plurality of wheels collectively identified by numeral 56 are mounted to bottom surface 54 of cradle 34. Cradle 34 rests on the top surface 40 of bridge 32 for movement therealong essential parallel to bore axis 22. In FIG. 1, cradle 34 is illustrated in a patient loading position. After a patient is positioned on surface 52, cradle 34 is typically repositioned such that cradle 34 resides generally within imaging area 26 in an imaging position (not illustrated).

Referring now to FIGS. 1 through 4, bracket 36 is generally mounted to the second surface 50 of main magnet 16 proximate a bottom magnet portion. Generally, when mounted to magnet 16, bracket 36 extends upwardly from magnet 16 toward imaging area 26 and forms at least one surface that contacts and supports the undersurface 42 of bridge 32 so that second end 46 of bridge 32 is supported and undersurface 42 is isolated from coil assembly 18.

To this end, the exemplary bracket 36 includes a "mustache" or yoke member 69 and first and second post members 70 and 72, respectively. Yoke member 69 includes a central arcuate segment 64 and first and second end segments 60 and 62, respectively. Arcuate segment 64 forms a top surface 66 and a bottom surface 68 and is concave along top surface 66. End segments 60 and 62 are separated by central segment 64 and each extends from an adjacent end of segment 64 away from undersurface 68. Segment 60 forms a mounting hole 74 while segment 62 forms a mounting hole 76. Holes 74 and 76 are spaced apart with respect to each other such that holes 74 and 76 are alignable with threaded apertures 80 and 82 on main magnet 16 to facilitate mounting.

Two mounting bolts 84 and 86 are provided which, to mount yoke member 69 to main magnet 16, pass through holes 76 and 74 and are received within threaded apertures 82 and 80, respectively. When so mounted, top surface 66 of yoke member 69 faces generally upwardly toward imaging area 26 and, like apertures 80 and 82, yoke 69 is symmetrically positioned with respect to a plane that divides magnet 16 into lateral halves. In the illustrated configuration yoke 69 has a length dimension L1 that is greater than bridge width W1 which provides additional stability to the supported bridge 32.

As best seen in FIG. 2, two post receiving apertures 90 and 92 are formed in top surface 66 of yoke member 69 and are generally vertically aligned. Apertures 90 and 92 are symmetrically formed within surface 66 so that a separate aperture is proximate each of end segments 60 and 62.

Post 70 is generally bolt shaped having a threaded shaft member (not separately numbered) and a head member 98 at a distal end. Post 70 is sized and threaded such that post 70 is threadably receivable within aperture 90 so that the distal end 98 extends generally upwardly and toward imaging area 26. Similarly, post 72 is generally bolt shaped having a threaded shaft that is receivable within aperture 92 and a distal head end 99 that extends generally upwardly toward imaging area 26. In the illustrated embodiment, the top surfaces 100 and 102 of post heads 98 and 99, respectively, form essentially upwardly facing support surfaces for receiving the undersurface of bridge 32 (see FIG. 2). As illustrated, heads 98 and 99 are received within recesses 110 and 112, respectively, and cooperate therewith to minimize lateral movement of bridge 32. Being threaded, posts 70 and 72 may be adjusted within apertures 90 and 92 to raise or lower heads 98 and 99 thereby adjusting the height of bridge second end 46 to an optimal level.

Importantly, for the purposes of the present invention, yoke member 69 and posts 70 and 72 are each, in at least one embodiment of the invention, formed of a non-flux generating material. In some cases the material used to form members 69 and posts 70 and 72 is a phenolic material that has suitable flux properties and has a high damping coefficient. Phenolic materials are particularly suitable for the present application as they have generally ideal properties. To this end, phenolic materials inhibit flux generation and generally have relatively high damping coefficients so that components constructed of phenolic materials reduce vibration transmission. Nevertheless, phenolic components are stiff enough to impart sufficient static support for bridge second end 46 that bridge 32 will not oscillate within imaging area 26.

Thus, referring again specifically to FIG. 1, it should be appreciated that the present invention generally isolates bridge 32 from gradient coil assembly 18. In MR configurations where gradient coil assembly 18 is isolated from main magnet 16 (i.e., as in the case of U.S. Pat. No. 6,160,399), bridge 32 is relatively well isolated from coil 18 and therefore patient comfort and image quality are increased appreciably by employing the present invention. For example, while the bracket is described as being relatively stiff it should be appreciated that a complaint damping material may be provided within the bracket supporting system (e.g., between bracket 69 and surface 50 or between surfaces 102, 100 and the undersurface of the bridge or between any other two adjacent surfaces) to further mitigate or dampen vibrations. In addition, while the bracket 69 is described as being secured to surface 50, it should be appreciated that bracket 69 may be secured to some other main magnet surface (e.g., an internal surface, etc.).

It should be understood that the methods and apparatuses described above are only exemplary and do not limit the scope of the invention, and that various modifications could be made by those skilled in the art that would fall under the scope of the invention.

To apprise the public of the scope of this invention, the following claims are made:

1. In an MR system including a main magnet, a gradient coil assembly and a patient support, the magnet having first and second oppositely facing surfaces and forming a bore that extends between the first and second surfaces along a bore axis, the coil assembly disposed within the bore about an imaging area, the support including a support member and a bridge having first and second ends, the support member supporting the first bridge end proximate the first surface, the bridge extending into and through the bore so that the second end is proximate the second surface, the bridge forming an essentially downwardly facing undersurface, the apparatus for supporting the bridge and comprising:

a bracket being disposed for fixable attachment to the main magnet such that the bracket extends toward the imaging area, the bracket forming at least one essentially upwardly facing support surface for receiving the bridge undersurface and supporting the bridge there above.

2. The apparatus of claim 1 wherein the bracket is disposed for fixable attachment to one of the first and second magnet surfaces.

3. The apparatus of claim 2 wherein the bracket is mountable to the second magnet surface.

4. The apparatus of claim 3 wherein the upwardly facing surface includes at least two upwardly facing surfaces and each of the upwardly facing surfaces is for receiving the bridge undersurface and supporting the bridge there above.

5. The apparatus of claim 4 wherein the bracket includes first and second post members that extend essentially upwardly to distal ends, the distal ends forming the first and second upwardly facing surfaces.

6. The apparatus of claim 2 wherein the bridge has a width dimension perpendicular to the bore axis, the bracket has a length dimension greater than the width dimension and the bracket is securable to the main magnet at opposite ends of the length dimension so as to have an essentially horizontal orientation.

7. The apparatus of claim 6 wherein the bracket includes a yoke member and at least one post member, the yoke member extending along the length dimension, the post member extending from the yoke member essentially perpendicular to the length dimension, the yoke member mountable to the main magnet so that the post member extends essentially upwardly from the yoke member to a distal end toward the imaging area, the distal end forming the upwardly facing support surface.

8. The apparatus of claim 7 wherein the at least one post member includes first and second post members extending essentially perpendicular to the length dimension, the distal ends of the first and second post members forming first and second upwardly facing support surfaces for supporting the undersurface at different locations.

9. The apparatus of claim 8 wherein the post members are spaced along the length dimension.

10. The apparatus of claim 9 wherein the yoke member and post members are formed of a low magnetic flux material.

11. The apparatus of claim 10 wherein the yoke member and post members are formed of a phenolic material.

12. The apparatus of claim 1 wherein the bracket is formed of a non low magnetic flux material.

13. The apparatus of claim 12 wherein the bracket is formed of a phenolic material.

14. In an MR system including a main magnet, a gradient coil assembly and a patient support, the magnet having first and second oppositely facing surfaces and forming a bore that extends between the first and second surfaces along a bore axis, the coil assembly disposed within the bore about an imaging area, the support including a support member and a bridge having first and second ends, the support member supporting the first bridge end proximate the first surface, the bridge extending into and through the bore so that the second end is proximate the second surface, the bridge forming an essentially downwardly facing undersurface and having an essentially horizontal width dimension perpendicular to the bore axis, the apparatus for supporting the bridge and comprising:

a yoke member having a length dimension greater than the width dimension;

first and second post members spaced apart along the yoke member length dimension and extending from the yoke member in essentially the same direction to first and second distal ends, respectively, the first and second distal ends forming first and second support surfaces, respectively; and means for fixably attaching the yoke member to the magnet second surface such that the yoke member length is essentially horizontal and the post members extend essentially vertically upwardly toward the imaging area to contact the bridge undersurface and support the bridge there above.

15. The apparatus of claim 14 wherein the means for attaching includes at least two bolts for securing opposite ends of the yoke member to the main magnet.

16. The apparatus of claim 15 wherein the yoke member is essentially concave upwardly.

17. The apparatus of claim 16 wherein the yoke member is formed of a phenolic material.

18. The apparatus of claim 16 wherein the post members are formed of a phenolic material.

19. The apparatus of claim 14 wherein a vertical plane through the bore axis defines first and second bridge halves and wherein the yoke member is fixably attachable to the magnet such that the first and second post members extend so as to support the first and second bridge halves, respectively.

20. The apparatus of claim 19 wherein each post includes a stainless steel rod having a distal end and a phenolic head member and wherein the yoke member is also formed of a phenolic material.

* * * * *